United States Patent [19]

Mizutani et al.

[11] 4,425,473

[45] Jan. 10, 1984

[54] POLYMERIZABLE BICYCLIC ORTHOESTER COMPOUNDS

[75] Inventors: Kiyokazu Mizutani, Inazawa; Takahisa Ogasawara, Tohkai, both of Japan

[73] Assignee: Toagosei Chemical Industry Co., Ltd., Tokyo, Japan

[21] Appl. No.: 230,537

[22] Filed: Feb. 2, 1981

[30] Foreign Application Priority Data

Feb. 4, 1980 [JP] Japan ................................. 55-11432
Feb. 4, 1980 [JP] Japan ................................. 55-11433
May 30, 1980 [JP] Japan ................................. 55-71333

[51] Int. Cl.³ .......................................... C07D 319/14
[52] U.S. Cl. ................................................ 549/363
[58] Field of Search ...................... 260/340.7; 549/363

[56] References Cited

U.S. PATENT DOCUMENTS

| | | | |
|---|---|---|---|
| 3,328,427 | 6/1967 | Melaas | 260/340.7 |
| 3,415,846 | 12/1968 | Kesslin et al. | 260/340.7 |
| 3,415,847 | 12/1968 | Talbott | 549/363 |
| 3,686,224 | 8/1972 | Deffner | 549/363 |
| 4,119,579 | 10/1978 | Capozza et al. | 260/340.7 |

FOREIGN PATENT DOCUMENTS

| | | | |
|---|---|---|---|
| 56-6108792 | 8/1981 | Japan | 549/363 |
| 56-6108793 | 8/1981 | Japan | 549/363 |

OTHER PUBLICATIONS

Barnes, R. A. et al., Bicyclic Ortho Esters by Direct Esterification, *J. Organic Chemistry*, 27, 90–93 (1962).
Hall, H. K., Jr. et al., 2,6,7-Trioxabicyclo[2.2.1]heptane, *J.A.C.S.*, 97, 3854 (1975).
Chem. Abstract 95:25664u (1981).

*Primary Examiner*—Ethel G. Love
*Attorney, Agent, or Firm*—Cooper, Dunham, Clark, Griffin & Moran

[57] ABSTRACT

Certain new derivatives of 2,6,7-trioxabicyclo[2,2,2]octane are found to undergo cationic ring-opening polymerization with positive expansion in volume or with no substantial change in volume, in contrast with known polymerizable compounds such as epoxides which present considerable shrinkage in volume on polymerization. These new bicyclic orthoester compounds can be prepared in a facile way known per se.

19 Claims, No Drawings

POLYMERIZABLE BICYCLIC ORTHOESTER COMPOUNDS

FIELD OF THE INVENTION

This invention relates to new bicyclic orthoester compounds which are derivatives of 2,6,7-trioxabicyclo[2,2,2]octane, to processes for the preparation thereof and to polymers derived from the compounds.

BACKGROUND OF THE INVENTION

Until recently most of known polymerizable compounds undergo positive shrinkage in volume on polymerization. Thus, for example, ethylene, vinyl chloride, methyl methacrylate and styrene will give rise to calculated shrinkages of 66.0% 34.4%, 21.2% and 14.5%, respectively, during the addition polymerization, as reported by William J. Bailey in J. Macromol. Sci. Chem. A9(5), pp. 849–865(1975). In cationic ring-opening polymerization of hitherto known monomers such as epoxides, considerable shrinkage in volume will also take place, although the shrinkage degree in that case will often be less than that observed during the addition polymerization. By way of reference, calculated shrinkages of some epoxides which will occur on ring-opening polymerization are as follows:

ethylene oxide: 23%; propylene oxide: 17%;
styrene oxide: 9%; epichlorohydrin: 12%;
2,2-dimethylethylene oxide: 20%.

The calculated shrinkages in volume under discussion are given by the equation:

$$\left[1 - \frac{\text{Specific gravity of monomer to be polymerized}}{\text{Specific gravity of polymer derived from monomer}}\right] \times 100$$

With such known monomers that will polymerize with an appreciable shrinkage in volume, there are problems that they provide no dimensional accuracy when used as molding materials, and that where used as casting materials, they impose strains due to the shrinkage on castings and cause reduction in adhesion to a mold as well as inaccuracy of the dimension of the castings. There are further problems in use that such monomers may lead to reduction in cohesion to a substrate or formation of warpage due to the internal strains when used as paints or adhesives.

Therefore, for a number of industrial applications including precision castings, strain-free composites, paints and adhesives, it is highly desirable to have monomers which will present nearly zero shrinkage or positive expansion in volume on polymerization.

Certain bicyclic monomers which may polymerize with expansion in volume have been reported by William J. Bailey as described in the afore-mentioned literature (J. Macromol. Sci. Chem.). According to the literature, the spiro orthocarbonate of the formula:

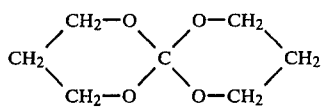

indicates a positive expansion of 2 to 17% upon its ring-opening polymerization.

We have closely studied in search of cyclic compounds which have not been described in literature and which will polymerize with no substantial change or appreciable expansion in volume. As a result, we have now discovered new bicyclic orthoester compounds which do, in most cases, indicate a considerable expansion during the ring-opening polymerization and which may be prepared from commercially available compounds in a facile way.

An object of this invention is to provide new bicyclic orthoester compounds which can undergo cationic ring-opening polymerization without substantial shrinkage or with positive expansion in volume. Another object of the invention is to provide processes for the preparation of these bicyclic compounds.

Further object of the invention is to provide polymers derived from the bicyclic compounds, the polymers having a specific gravity of substantially equal to or lower than that of the monomer compounds from which the polymers have been derived.

Other objects and advantages of this invention will become apparent from the following descriptions.

DETAILED DESCRIPTION OF THE INVENTION

According to an aspect of this invention, there is provided a bicyclic orthoester compound of the general formula:

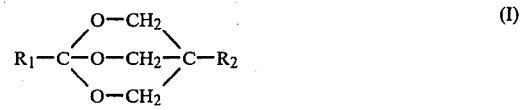

(I)

wherein $R_1$ is vinyl group (—CH=CH$_2$) when $R_2$ is a lower alkyl group; or $R_1$ is a lower alkyl group when $R_2$ is methylol group (—CH$_2$OH), a group of —CH$_2$—OCONH—Y or a group of

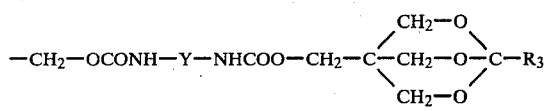

where $R_3$ is the same alkyl group as $R_1$ and Y is an organic mono- and di-isocyanate residue.

Some 2,6,7-trioxabicyclo[2,2,2]octane derivatives related to the compounds of this invention, typically 4-methyl-1-trifluoromethyl-2,6,7-trioxabicyclo[2,2,2]octane are described in J. Org. Chem. 27, 90–93 (1962). However, this literature neither discloses the compounds corresponding to general formula (I) as defined above nor suggests the polymerizability of the bicyclo orthoester compounds.

A specific class of the compounds of this invention include those of the following formula:

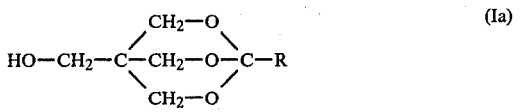

(Ia)

wherein R is a lower alkyl group.

The term "lower alkyl" used herein means an alkyl containing 1 to 4 carbon atoms, for example, methyl, ethyl, propyl, isopropyl and butyl.

The compounds of formula (Ia) may be prepared by the reaction between pentaerythritol and a trialkyl orthoacylate of the formula:

$$R-C(-O-R')_3 \quad (II)$$

where R is as defined above and R' is an alkyl, preferably lower alkyl group. The reaction scheme is shown as follows:

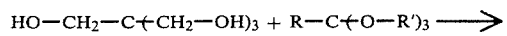

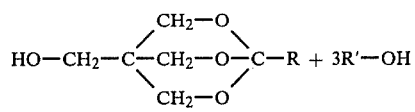

The above reaction is usually carried out in a suitable solvent such as di-n-octyl phthalate or di-n-butyl phthalate in the presence of a catalyst, for example, p-toluenesulfonic acid. The reaction may generally be effected at an elevated temperature, for example, of 100° to 140° C. under an atmosphere of an inert gas such as nitrogen. The reagents may be reacted with each other at an equimolar ratio, although either reagent may be used in slight excess.

The extent to which the reaction has proceeded can be monitored by measuring the quantity of the alcohol distilled off or by analyzing the resulting reaction solution, for example, by liquid chromatography. The desired product may be isolated from the reaction mixture by a conventional technique, for instance, by distillation under reduced pressure or fractional crystallization depending upon the nature of the product.

The compounds of formula (II) are known per se or may be made by a known method as described in J.A.C.S., 64, 1825-1827 (1942).

Another class of the compounds of this invention include those of the formula:

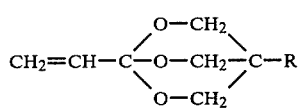

where R is as defined hereinabove.

The compounds of formula (Ib) may be prepared by the dehydrohalogenation of a compound of the formula:

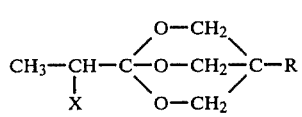

wherein R is as defined above and X is a halogen atom such as chlorine, bromine or iodine, as shown in the following scheme.

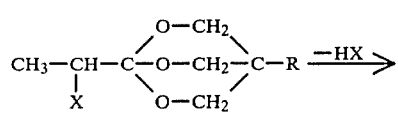

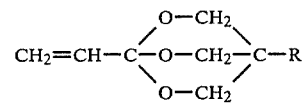

The dehydrohalogenation reaction may generally be carried out in an appropriate solvent such as tetrahydrofuran with the aid of an alkali such as sodium or potassium t-butoxide. The extent to which the reaction has proceeded can easily be monitored by analysis of the resulting reaction solution, for example, by liquid chromatography. The desired product may be isolated from the reaction solution by a conventional procedure, for example, by pouring the reaction solution into water, extracting the solution with an organic solvent such as ethyl ether or benzene, drying and evaporating the organic extract and distillating the residue under reduced pressure.

The compounds of formula (III) may be made by reacting a 1,1,1-trialkoxy-2-halopropane with a 2-alkyl-2-hydroxymethylpropane-1,3-diol, e.g. trimethylolpropane or trimethylolethane according to the following scheme:

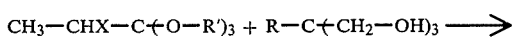

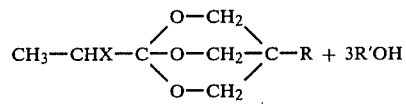

The above reaction may be effected in the same manner as already mentioned for the preparation of the compound (Ia).

Further specific class of the compounds which are included within the scope of general formula (I) correspond to the formula:

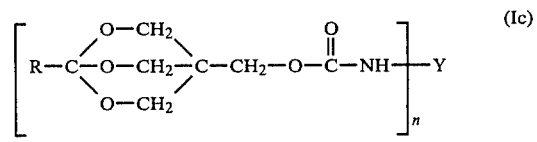

wherein R and Y are as defined hereinbefore and n is 1 or 2.

In formula (Ic), group Y is a residue derived from an organic monoisocyanate (Y—NCO) or diisocyanate (OCN—Y—NCO). When Y is a monovalent group (n=1), it may be an alkyl, aryl, alkenyl, aralkyl, alkaryl or cycloalkyl group, these groups preferably containing up to 12 carbon atoms and being optionally substituted, for example, by one or more of halogens and alkoxy groups. When Y is a divalent group (n=2), it may be an optionally substituted (e.g. halogen- or alkoxy-substituted) alkylene, arylene, aralkylene, alkarylene or cycloalkylene group or a group of the formula:

$$-A-A- \text{ or } -A-B-A-$$

where each A is phenylene or cycloalkylene which may be substituted, for example, by one or more of halogens and alkoxy groups and B is an alkylene group or oxygen atom.

The compounds of formula (Ic) may be prepared by the reaction between a compound of above formula (Ia) and an organic monoisocyanate (Y—NCO) or an organic diisocyanate (OCN—Y—NCO).

Typical examples of the organic monoisocyanate to be reacted with the compound (Ia) include aliphatic monoisocyanates such as methyl isocyanate, ethyl isocyanate, n-propyl isocyanate, n-butyl isocyanate, hexyl isocyanate, chloroethyl isocyanate, chloropropyl isocyanate, chlorohexyl isocyanate, chlorobutoxypropyl isocyanate and octadecyl isocyanate; and aromatic monoisocyanates such as phenyl isocyanate, o-, m- and p-chlorophenyl isocyanate, benzyl isocyanate, naphthyl isocyanate, o-ethylphenyl isocyanate and dichlorophenyl isocyanate.

Typical examples of the organic diisocyanate include tetramethylene diisocyanate, hexamethylene diisocyanate, lysine diisocyanate, dimer acid diisocyanates, cyclohexane diisocyanate, 2,4- and 2,6-tolylene diisocyanate, diphenylmethane-4,4'-diisocyanate, m- and p-xylylene diisocyanate, dicyclohexylmethane-4,4'-diisocyanate, dianisidine diisocyanate, tolidine diisocyanate, 1,5-naphthalene diisocyanate, diphenylether-4,4'-diisocyanate and diphenylene-4,4'-diisocyanate.

The reaction to produce the compounds of formula (Ic) may be carried out at a temperature in the range 20° to 100° C., preferably 50° to 80° C. in the presence or absence of a catalyst. The catalyst which may be used includes organic amines and organometallic compounds which are known in the art to be employed for urethane formation. As the organic amines are preferred tertiary amines since primary and secondary amines will react with the isocyanate group (—NCO) present in the reaction system to transform into inactive forms. As the organometallic compounds, organotin compounds are particularly suitable. Specific examples of the usable catalyst include N,N,N',N'-tetramethyl-1,3-butanediamine, triethylenediamine, N-methylmorpholine, dibutyltin dilaurate, dibutyltin di(2-ethylhexoate), stannous 2-ethylcaproate and dibutyltin oxide.

The catalyst is generally used in an amount of 0.0001 to 0.5% by weight of organic isocyanate.

The reaction as discussed just above may be performed without any solvent but conveniently with the aid of a solvent which is inert to isocyanate group. Examples of the solvent to be suitably used include aromatic hydrocarbons such as benzene and toluene; halogenated hydrocarbons such as methylene chloride, ethylene chloride and carbon tetrachloride; esters such as ethyl acetate and butyl acetate; ethers such as diisopropyl ether and di-n-butyl ether; and ketones such as acetone and methyl ethyl ketone.

As already stated, it has been found that the compounds of general formula (I) can undergo cationic polymerization with nearly zero shrinkage or positive expansion in volume to produce ring-opened polymers. It is believed, without prejudice to this invention, that the cationic polymerization will occur according to the following mechanism:

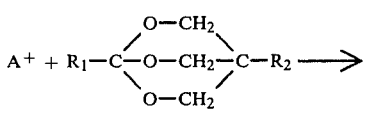

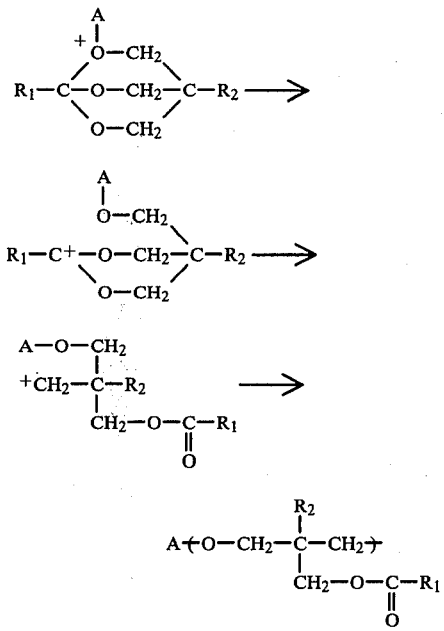

It is noteworthy and unexpected that the compounds of formula (I), particularly those of formula (Ia) give a positive expansion upon polymerization, in view of the fact that the most related compound of the formula:

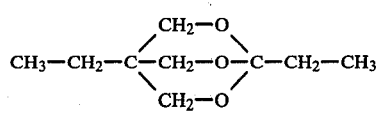

gives no substantial expansion on its cationic polymerization. The above known compound is referred to in J. Org. Chem., 27, 90–93 (1962).

According to a further aspect of this invention, therefore, there is provided a polymer consisting essentially of the repeated structural units represented by the formula:

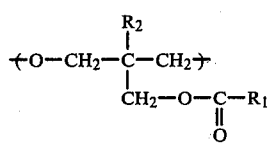

wherein $R_1$ is vinyl group when $R_2$ is a lower alkyl group; or $R_1$ is a lower alkyl group when $R_2$ is hydroxylmethyl group or a group of —$CH_2$—OCONH—Y where Y is an organic monoisocyanate residue, and which is the product of the cationic ring-opening polymerization of a compound having the formula:

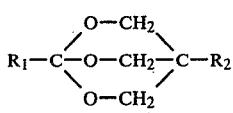

wherein $R_1$ and $R_2$ are as defined just above.

The cationic polymerization of the compounds (I) may be carried out by a conventional technique known per se, for example, by irradiation with ultraviolet rays, infrared rays or microwaves or application of heat in the presence of a suitable catalyst (initiator).

Examples of the catalyst which may be used for ultraviolet cationic polymerization include: aromatic diazonium salts such as $\phi-N^+\equiv N.PF_6^-$ and $\phi-N^+\equiv N.BF_4^-$; aromatic halonium salts such as $\phi-I^+-\phi.BF_4^-$; aromatic onium salts of the elements of Group Va of the Periodic Table such as

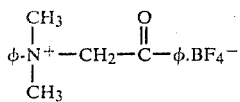

and aromatic onium salts of the elements of Group VIa of the Periodic Table such as

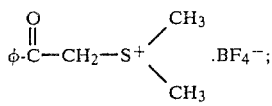

dicarbonyl chelates of the Group IIIa-Va elements of the Periodic Table such as

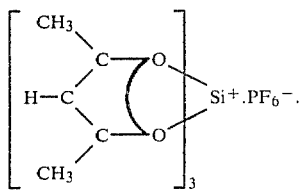

These initiators may be used alone or in combination.

As the polymerization initiator usable for other modes of cationic polymerization by means of heat energy such as infrared rays, heat or microwaves, there may be mentioned Lewis acids such as $BF_3$, $FeCl_3$, $SnCl_4$, $SbCl_5$, $SbF_3$, $TiCl_4$, etc.; coordination compounds of Lewis acids with compounds bearing O, S or N such as $BF_3OEt_2$, $BF_3$-aniline complexes, etc.; oxonium salts, diazonium salts and carbonium salts of Lewis acids; halides, mixed halides; and perhalogeno-acid derivatives. These initiators may be used alone or in combination.

The initiator is generally used in an amount of 0.001 to 10% by weight, preferably 0.1 to 5% by weight based on the weight of the monomer to be polymerized. The polymerization temperature is not critical, although it is generally between room temperature (c.a. 25° C.) and 200° C.

The cationic polymerization is usually carried out in the absence of any solvent but may be conducted, if desired, in the presence of a suitable solvent which must not react with cations present during the propagation step to prevent the cations from reduction in activity. Examples of the solvent to be used as the case may be include aliphatic hydrocarbons such as hexane and octane; aromatic hydrocarbons such as toluene and xylene; and halogenated hydrocarbons such as methylene chloride and 1,1-dichloroethane.

With the compounds of above formula (Ic) in which n is 2 and thus Y is an organic diisocyanate residue, the cationic polymerization thereof will produce crosslinked polymers as represented by the formula:

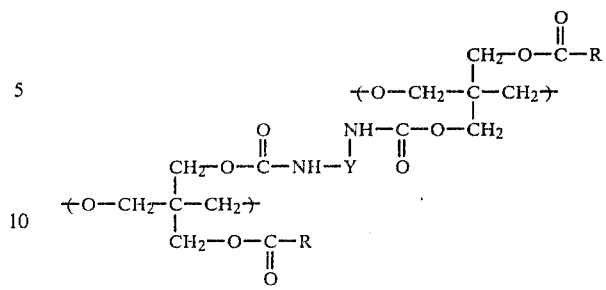

With the compounds of above formula (Ib) carrying 1-vinyl group, the cationic polymerization thereof will frequently cause not only the opening of the bicyclo orthoester ring but also the concurrent polymerization of the vinyl group to produce a crosslinked polymer comprising the repeated structural units which may be represented by the formula:

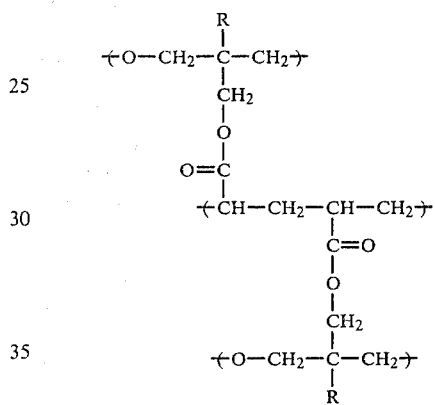

Moreover, the compounds of formula (Ib) can undergo radical polymerization with the aid of a radical polymerization initiator whereby the vinyl group is polymerized to give a polymer consisting essentially of the repeated units represented by the formula:

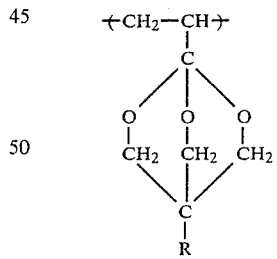

wherein R is as defined hereinbefore.

Further polymerization of this polymer in the presence of a cationic polymerization initiator as already mentioned for the cationic polymerization of the compounds (I) would result in opening of the pendant bicyclo orthoester ring to produce a crosslinked polymer.

The radical polymerization of the compounds (Ib) may be carried out by any conventional technique, for example, by irradiation with ultraviolet rays, infrared rays, electron rays or microwaves or application of heat.

In the case of ultraviolet radical polymerization, a radical photo-initiator is generally used. Among the radical photo-initiators to be used for this purpose are, for example, carbonyl compounds such as acetophenone, 2,2-dimethoxy-2-phenylacetophenone, 2,2-diethoxyacetophenone, 4'-isopropyl-2-hydroxy-2-methyl-propiophenone, 2-hydroxy-2-methyl-propiophenone, 4,4'-bis-diethylaminobenzophenone, benzophenone, methyl-(o-benzoyl)-benzoate, 1-phenyl-1,2-propanedione-2-(o-ethoxy-carbonyl)-oxime, 1-phenyl-1,2-propanedione-2-(o-benzoyl)-oxime, benzoin, benzoin methyl ether, benzoin ethyl ether, benzoin isopropyl ether, benzoin isobutyl ether or benzoin octyl ether, benzil or diacetyl; anthraquinone, xanthone or their derivatives such as methylanthraquinone, chloroanthraquinone, chlorothioxanthone, 2-methylthio-xanthone or 2-isopropylthioxanthone; sulfur compounds such as diphenyl sulfide, diphenyl disulfide or dithiocarbamate; α-chloromethylnaphthalene; and anthracene. These initiators maybe used alone or in combination.

In the case of radical polymerization by means of heat energy such as infrared rays, heat or microwaves, it is possible to use any known type of radical polymerization initiator provided that it is capable of producing radicals by decomposition due to the heat energy. For instance, there may be used an organic peroxide such as di-tert-butyl peroxide, 2,5-dimethyl-2,5-di(tert-butyl-peroxide)hexane, tert-butyl hydroperoxide or tert-butyl peroxybenzoate; an azo compound such as azobisbutylonitrile; and inorganic peroxide such as ammonium persulfate or potassium persulfate. These initiators may also be used alone or in combination.

The radical polymerization by means of ionizing radiation such as electron beams or X-rays is usually effected in a non-catalytic system.

The radical polymerization initiator is generally used in an amount of 0.01 ot 10% by weight, preferably 0.1 to 5% by weight based on the monomer to be polymerized. The polymerization temperature is not critical, although it is generally between room temperature (c.a. 25° C.) and 200° C.

The radical polymerization is usually carried out in the absence of any solvent but may be conducted, if desired, in the presence of a suitable inert solvent.

Preferred examples of the solvent which may be used include toluene, xylene, ethyl acetate, N,N-dimethylformamide, chloroform and carbon tetrachloride.

The compounds of formula (I) according to this invention have wide applications, for example, as molding and casting materials and materials for adhesives and paints by taking advantage of their properties that they can polymerize with no change in volume or generally with appreciable expansion in volume as discussed hereinbefore. In particular, the polymers derived from the compounds of the invention exhibit a good adhesion to various substances such as metals and notably glass and thus they are highly effective as adhesives for these substances.

This Example is further illustrated but not limited by the following Examples, in which the specific gravity of the products was measured by Method A, B, C or D as follows:

Method A: measured at 25° C. by gradient tube method using B-type direct-reading specific gravimeter (manufactured by Shibayama Kagaku Kikai Seisakujo, Japan) wherein a sample of the product was degassed in an aqueous solution of potassium carbonate and placed in a gradient tube prepared from aqueous potassium carbonate solution.

Method B: measured at 25° C. by gradient tube method wherein a sample of the product was heated above its melting point, then degassed and placed in the same gradient tube as in Method A.

Method C: measured at 25° C. using a specific gravity bottle.

Method D: measured at 25° C. using an air-comparative gravimeter of 930 type (manufactured by Beckmann Japan Co., Ltd.).

The melting point of the products was measured using a differential scanning calorimeter of bench standard type (manufactured by Rigaku Denki K.K., Japan).

The molecular weight given for the polymers produced was calculated as polystyrene-reduced weight average molecular weight from the liquid chromatographic analysis using the conditions:

Apparatus; HLC-80/A manufactured by Toyo Soda Industry Co., Ltd.,
Column; Two TSK Gel-GMH columns or TSK Gel (G 3000 H+G 2000 H) columns,
Eluent; Tetrahydrofuran
Flow rate; 1 ml/min.

The expansion in volume which occurred upon the polymerization was calculated by the equation:

$$\left[ \frac{\text{Specific gravity of monomer to be polymerized}}{\text{Specific gravity of polymer derived from monomer}} - 1 \right] \times 100$$

EXAMPLE 1

Preparation of 1-ethyl-4-hydroxymethyl-2,6,7-trioxabicyclo [2,2,2] octane

In a 2 l flask were placed 272 g (2 moles) of pentaerythritol, 352 g (2 moles) of triethyl orthopropionate, 345 g of di-n-octyl phthalate and 2 g of p-toluenesulfonic acid as catalyst and the resultant mixture was heated to a temperature of 110° C. and slowly raised to 140° C. with stirring under nitrogen atmosphere. The rise in temperature was accompanied by formation of ethanol, which was distilled off. After the reaction for 3.5 hours, there was obtained 261 g of the distillate predominantly comprising ethanol.

Subsequently, 10 g of anhydrous potassium carbonate was added to the reaction solution to neutralize the catalyst, followed by centrifugal separation to remove a precipitate involving unreacted starting material (pentaerythritol) and the neutralized catalyst from a supernatant. The latter was distilled under reduced pressure to give 233 g (67%) of the title compound with a boiling point of 97°–100° C./0.2 mmHg and a specific gravity of 1.204 (Method C).

Analysis: Calcd. for $C_8H_{14}O_4$: C, 55.2; H, 8.1. Found: C, 55.0; H, 8.0.

Nuclear magnetic resonance spectroscopy ($CDCl_3$): δ(ppm); 4.0 (6H, s), 3.4 (2H, s), 2.8 (1H, s), 1.7 (2H, q), 0.9 (3H, t).

Infrared spectroscopy (liquid film): 3480 $cm^{-1}$ (—OH), 930, 1050, 1100 $cm^{-1}$ (C—O—C).

EXAMPLE 2

Preparation of 1-methyl-4-hydroxymethyl-2,6,7-trioxabicyclo [2,2,2] octane

Into a 2 l flask were charged 162 g (1 mole) of triethyl orthoacetate, 136 g (1 mole) of pentaerythritol, 250 g of di-n-octyl phthalate and 0.5 g of p-toluenesulfonic acid as catalyst. The mixture was heated to 135° C. with stirring under nitrogen atmosphere and allowed to stand at this temperature for 4 hours, resulting in formation of 126 g of a distillate based on ethanol.

To the resultant reaction solution was added 1 g of triethylamine to neutralize the catalyst and the mixture was then allowed to stand at ambient temperature overnight to precipitate crystals comprising the desired product and unreacted starting material (pentaerythritol). The crystals separated were washed three times with cyclohexane (which is a non-solvent for the desired product) to remove the solvent (di-n-octyl phthalate), and then dissolved in acetone followed by filtration to remove acetone-insoluble matters. After the acetone was evaporated off from the filtrate, the residue was recrystallized from chloroform in three replicates to give 25 g (16%) of the title compound in the form of white powder which had a melting point of 113°–115° C. and a specific gravity of 1.37 (Method D).

Analysis: Calcd. for $C_7H_{12}O_4$: C, 52.5; H, 7.6. Found: C, 52.4; H, 7.7.

N.M.R. spectra (deutero acetone): δ(ppm); 4.1 (6H, s), 3.5 (2H, d), 1.3 (3H, s).

I.R. spectra (KBr disc): 3400 cm$^{-1}$ (—OH), 980, 1040, 1135 cm$^{-1}$ (C—O—C).

EXAMPLE 3

Preparation of 1-vinyl-4-ethyl-2,6,7-trioxabicyclo[2,2,2] octane (a) 1,1,1-Triethoxy-2-bromopropane A solution of 176 g (1 mole) of triethyl orthopropionate and 96 g (1.2 moles) of pyridine in 1 l of carbon tetrachloride was placed in a 2 l flask and 160 g (1 mole) of bromine was slowly added over two hours to the solution under ice-cooling. The resultant reaction mixture was allowed to stand at room temperature for one day to form a precipitate, which was then filtered off. The filtrate was concentrated by evaporation of the solvent and the residue was subjected to distillation under reduced pressure to afford 206 g (81%) of 1,1,1-triethoxy-2-bromopropane with a boiling point of 85° C./13 mmHg.

Analysis: Calcd. for $C_9H_{19}O_3Br$: C, 42, 35; H, 7.45; Br, 31.37. Found: C, 42, 27; H, 7.40; Br, 31.60.

I.R. (liquid film): 1120 cm$^{-1}$ (ether), 1245 cm$^{-1}$ (C-Br).

N.M.R. (CDCl$_3$): δ(ppm); 1.18 (9H, 3CH$_3$—), 1.69 (3H, —CH$_3$), 3.63 (6H, 3—CH$_2$—), 4.17 (1H, BrCH).

(b) 1-Bromoethyl-4-ethyl-2,6,7-trioxabicyclo[2,2,2] octane 25.5 g (0.1 moles) of the product obtained in step (a) above, 13.4 g (0.1 moles) of trimethylolpropane and 0.05 g of p-toluenesulfonic acid were placed in a flask fitted with a Dean & Stark condenser and the contents of the flask were heated at 140° C. for about 2 hours. The reaction was stopped when a theoretical amount of ethyl alcohol was evaporated off, after which the reaction solution was distilled under reduced pressure using a Vigreaux distillation column to yield 16 g (63%) of the desired product having a boiling point of 81°–83° C./0.1 mmHg.

Analysis: Calcd. for $C_8H_{15}O_3Br$: C, 43.03; H, 5.98; Br, 31.87. Found: C, 43.10; H, 5.83; Br, 31.96.

I.R. (liquid film): 1122 cm$^{-1}$ (ether), 1250 cm$^{-1}$ (C-Br).

N.M.R. (CDCl$_3$): δ(ppm); 0.7–1.6 (5H, Et), 1.68 (3H, Me), 3.92 (6H, —CH$_2$O—), 3.7–4.2 (1H, BrCH).

(c) 1-Vinyl-4-ethyl-2,6,7-trioxabicyclo[2,2,2] octane 25 g (0.1 moles) of the product obtained in step (b) above was added dropwise over about one hour at room temperature to a solution of 11 g (0.1 moles) of potassium t-butoxide in 100 ml of tetrahydrofuran placed in a 250 ml flask. The mixture was heated at reflux temperature for 5 hours and the reaction solution obtained was poured into water. The resulting solution was extracted with ethyl ether and the organic layer was dried over anhydrous magnesium sulfate and concentrated by evaporation of the ether. The residue was distilled under reduced pressure to give 14 g (83%) of the title compound with a boiling point of 68°–72° C./2 mmHg and a specific gravity of 1.216 (Method D).

Analysis: Calcd. for $C_9H_{14}O_3$: C, 63.5; H, 8.2. Found: C, 63.4; H, 8.3.

I.R. (liquid film): 1100 cm$^{-1}$ (C—O—C), 990 and 1420 cm$^{-1}$ (CH$_2$=CH—).

N.M.R. (CDCl$_3$):

δ(ppm); 0.6–1.4 (5H, Et), 4.0 (6H, —CH$_2$—O—), 5.2–6.0 (3H, CH$_2$=CH—).

The following Examples 4–12 illustrate the preparation of urethane bicyclo ortho ester compounds of this invention.

EXAMPLE 4

20 ml of dry toluene and 8.7 g (0.05 moles) of 1-ethyl-4-hydroxymethyl-2,6,7-trioxabicyclo[2,2,2] octane (prepared as described in Example 1) were added to 3.55 g (0.05 moles) of ethyl isocyanate, followed by 0.005 g of dibutyltin dilaurate as catalyst and the resultant mixture was kept aside at 60° C. for 4 hours. The reaction solution was concentrated by evaporation of the solvent and subjected to distillation under reduced pressure to yield 7.1 g (58%) of the compound having the following structure.

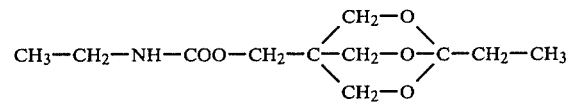

B.p. 125° C./0.15 mmHg; M.p. 76°–79° C.

Specific gravity; 1.25 (Method C).

I.R. (NaCl disc): 3300, 1720, 1540, 1250 cm$^{-1}$ (urethane).

N.M.R. (CDCl$_3$): δ(ppm); 0.92 (3H, t, —CH$_3$), 1.12 (3H, t, —CH$_3$), 1.65 (2H, q, C—CH$_2$—C), 3.12 (2H, N—CH$_2$), 3.81 (2H, s, COO—CH$_2$), 3.94 (6H, S, O—CH$_2$), 5.75 (1H, —NH).

EXAMPLE 5

30 ml of dry toluene and 8.7 g (0.05 moles) of 1-ethyl-4-hydroxymethyl-2,6,7-trioxabicyclo[2,2,2] octane were added to 5.95 g (0.05 moles) of phenyl isocyanate, followed by 0.005 g of dibutyltin dilaurate as catalyst and the mixture was kept aside at 70° C. for 4 hours. The reaction solution obtained was concentrated to dryness to give a solid residue, which was then crystallized from methylene chloride-cyclohexane to yield 8.5 g (58%) of the compound of the following structure.

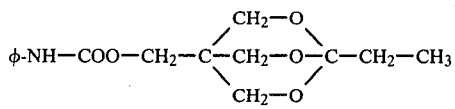

M.p. 123°–125° C.
Specific gravity; 1.33 (Method A).
I.R. (KBr disc): 3320, 1725, 1540, 1215 cm$^{-1}$ (urethane).
N.M.R. (CDCl$_3$): δ(ppm); 0.93 (3H, t, —CH$_3$), 1.70 (2H, q, C—CH$_2$—C), 3.91 (2H, s, COO—CH$_2$), 3.99 (6H, s, O—CH$_2$), 6.9–7.4 (5H, φ—H).

EXAMPLE 6

Following the procedure as described in Example 5 but starting from 3.20 g (0.02 moles) of 1-methyl-4-hydroxymethyl-2,6,7-trioxabicyclo[2,2,2] octane (prepared as noted in Example 2), there was obtained 2.3 g (41%) of the corresponding 1-methyl compound after crystallization from toluene.

Structural formula:

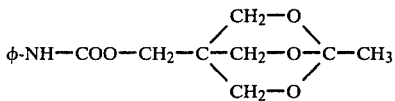

M.p. 147°–149° C.
Specific gravity; 1.33 (Method A).
I.R. (KBr disc): 3380, 1715, 1530, 1220 cm$^{-1}$ (urethane).
N.M.R. (deutero acetone): δ(ppm); 1.36 (3H, s, —CH$_3$), 3.99 (8H, s, COO—CH$_2$, O—CH$_2$), 6.9–7.4 (5H, m, φ—H), 8.5–8.7 (1H, —NH).

EXAMPLE 7

25 ml of ethyl acetate and 8.7 g (0.05 moles) of 1-ethyl-4-hydroxymethyl-2,6,7-trioxabicyclo[2,2,2] octane were added to 4.2 g (0.025 moles) of hexamethylene diisocyanate, followed by 0.003 g of dibutyltin dilaurate as catalyst and the mixture was allowed to stand at 70° C. for 4 hours. The resulting reaction solution was evaporated to dryness to leave a solid residue, which was crystallized from ethyl acetate/cyclohexane to give 5.3 g (41%) of the compound of the formula:

wherein each Q stands for the group of

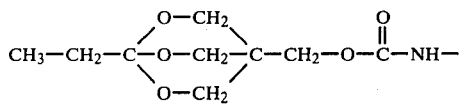

M.p. 108°–111° C.
Specific gravity; 1.221 (Method B).
I.R. (NaCl disc): 3340, 1720, 1535, 1255 cm$^{-1}$ (urethane).
N.M.R. (CDCl$_3$): δ(ppm); 0.93 (6H, t, —CH$_3$), 1.1–1.8 (12H, C—CH$_2$—C), 3.11 (4H, N—CH$_2$), 3.83 (4H, s, COO—CH$_2$), 3.96 (12H, s, O—CH$_2$), 5.3 (2H, —NH).

EXAMPLE 8

Into a four-necked flask were charged 12.2 g (0.07 moles) of 2,4-tolylene diisocyanate, 30 ml of dry toluene and 0.008 g of dibutyltin dilaurate and the contents of the flask were heated to 70° C. on an oil bath. 24.4 g (0.14 moles) of 1-ethyl-4-hydroxymethyl-2,6,7-trioxabicyclo[2,2,2] octane was then added dropwise over about one hour with stirring under nitrogen atmosphere. After completion of the addition, the resultant mixture was kept aside at a temperature of nearly 70° C. for 3.5 hours and the reaction solution was evaporated to dryness. The residue was crystallized from methylene chloride/cyclohexane to give 28.9 g (79%) of the compound of the formula:

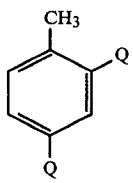

wherein each Q stands for the same group as in Example 7.
M.p. 112°–114° C.
Specific gravity; 1.282 (Method B).
I.R. (KBr disc): 3300, 1720, 1530, 1220 cm$^{-1}$ (urethane).
N.M.R. (CDCl$_3$): δ(ppm); 0.93 (6H, t, —CH$_3$), 1.70 (4H, q, C—CH$_2$—C), 2.16 (3H, s, φ—CH$_3$), 3.92 3.97 (16H, s, O—CH$_2$, COO—CH$_2$), 6.8–7.8 (3H, φ—H).

EXAMPLE 9

30 ml of dry toluene, 8.7 g (0.05 moles) of 1-ethyl-4-hydroxymethyl-2,6,7-trioxabicyclo[2,2,2] octane and 0.003 g of dibutyltin dilaurate were added to 6.25 g (0.025 moles) of diphenylmethane-4,4'-diisocyanate (referred to as MDI) and the mixture was kept aside at 75° C. for 6 hours. The reaction solution obtained was concentrated to dryness to give a solid residue, which was then crystallized from methylene chloride-cyclohexane to yield 6.13 g (41%) of the compound of the formula:

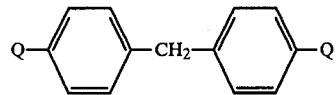

wherein Q is as defined in Example 7.
M.p. 168° C.
Specific gravity; 1.274 (Method B).
I.R. (KBr disc): 3310, 1720, 1530, 1215 cm$^{-1}$ (urethane).
N.M.R. (C$_5$D$_5$N): δ(ppm); 1.07 (6H, t, —CH$_3$), 1.89 (4H, q, C—CH$_2$—C), 3.8–4.3 (18H, φ—CH$_2$, COO—CH$_2$, O—CH$_2$), 7.1–8.0 (8H, φ—H).

EXAMPLE 10

The procedure of Example 9 was repeated but using 6.55 g (0.025 moles) of dicyclohexylmethane-4,4'-diisocyanate instead of MDI. There was thus obtained 11.4 g (75%) of the compound of the formula:

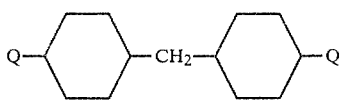

wherein Q is as defined in Example 7.
Softening point; 104°–107° C.
Specific gravity; 1.198 (Method B).
I.R. (NaCl disc): 3340, 1720, 1540 cm$^{-1}$ (urethane).
N.M.R. (CDCl$_3$): δ(ppm);

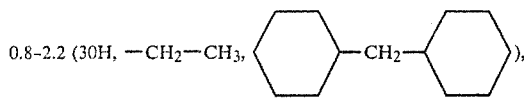

3.4–3.8 (2H, N—CH), 3.80 (4H, COO—CH$_2$), 3.94 (12H, O—CH$_2$), 4.4–4.8 (2H, C—NH).

EXAMPLE 11

The procedure of Example 9 was repeated but using 5.55 g (0.025 moles) of 3-isocyanatemethyl-3,5,5-trimethyl cyclohexyl isocyanate instead of MDI. There was thus obtained 11.7 g (82%) of the compound of the formula:

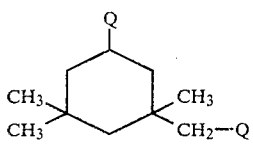

wherein each Q is as defined in Example 7.
Softening point; 88°–91° C.
Specific gravity; 1.200 (Method B).
I.R. (KBr disc): 3330, 1720, 1530, 1225 cm$^{-1}$ (urethane).
N.M.R. (CDCl$_3$): δ(ppm); 0.6–1.5 (19H, —CH$_3$, —CH$_2$ in the cyclohexane ring), 1.5–1.9 (6H, C—CH$_2$—C, —CH$_2$ in the cyclohexane ring), 2.8–3.0 (2H, N—CH$_2$), 3.5–4.1 (17H, N—CH, COO—CH, O—CH$_2$), 4.6–5.1 (2H, N—H).

EXAMPLE 12

By the same procedure as described in Example 5 except using 4.35 g (0.025 moles) of the 1-ethyl orthoester compound and replacing phenyl isocyanate by 2.10 g (0.0125 moles) of hexamethylene diisocyanate, there was obtained 4.8 g (79%) of the compound of the formula:

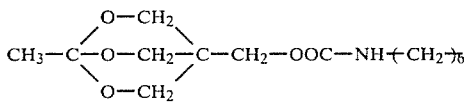

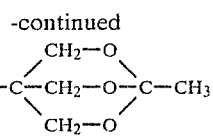

M.p. 141° C.
Specific gravity; 1.258 (Method B).
I.R. (KBr disc) 3370, 1700, 1520, 1250 cm$^{-1}$ (urethane).
N.M.R. (CDCl$_3$): δ(ppm); 1.2–1.7 (14H, —CH$_3$, C—CH$_2$—C), 3.12 (4H, N—CH$_2$), 3.84 (4H, COO—CH$_2$), 3.97 (12H, O—CH$_2$), 4.8 (2H, —NH).

The following Examples illustrate the polymerization of the bicyclo ortho ester compounds prepared in the aforegoing Examples.

EXAMPLE 13

5.0 g of the monomer compound prepared in Example 1 was placed in a tube, into which was added as catalyst 3 molar %, based on the monomer, of BF$_3$O(C$_2$H$_5$)$_2$. The tube was sealed and heated at 70° C. for 17 hours to perform the polymerization. There was thus obtained a polymer in the form of viscous liquid.

The polymer had a weight average molecular weight of about 4000 and a specific gravity of 1.186 (Method C). This specific gravity indicates that a calculated expansion in volume of about 1.5% had occurred during the polymerization.

The polymer was identified by infrared spectroscopy showing the appearance of the absorptions at 1190 cm$^{-1}$ and 1730 cm$^{-1}$ due to ester group

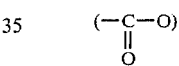

and the disappearance of the absorptions at 930 cm$^{-1}$ and 950 cm$^{-1}$ atributed to the ether group (C—O—CH$_2$) of the bicyclo ester ring in the monomer compound.

EXAMPLES 14–27

The general procedure as described in Example 13 was repeated but under the modified polymerization conditions as set out in the table below, where the second column indicates the reference number of Example in which the starting monomer was prepared. The weight average molecular weight (M.W.), specific gravity (S.G.), calculated expansion in volume (E.V.) and morphology of each polymer produced are also shown in the table.

In Example 15, the infrared spectroscopy of the resultant polymer indicated the existence of the absorptions at 1190 and 1720 cm$^{-1}$ due to the ester group formed by the opening of the bicyclo orthoester ring and, on the other hand, indicated the disappearance of the absorption at 940 cm$^{-1}$ attributed to the ether group (C—O—CH$_2$) of the bicyclo orthoester ring and also the substantial disappearance of the absorption at 1420 cm$^{-1}$ attributed to the vinyl group in the monomer.

| Example No. | Monomer (Example No.) | Catalyst (molar % or wt % based on the monomer) | Polymerization Temp. (°C.) | Polymerization Time (hr.) | Polymer Morphology | Polymer M.W. | Polymer S.G. (Method) | Polymer E.V. |
|---|---|---|---|---|---|---|---|---|
| 14 | 2 | BF$_3$O(C$_2$H$_5$)$_2$ (3 molar %) | 110 | 3 | Solid | c.a. 400 | 1.25 (C) | 9% |

-continued

| Example No. | Monomer (Example No.) | Catalyst (molar % or wt % based on the monomer) | Polymerization Temp. (°C.) | Polymerization Time (hr.) | Polymer Morphology | M.W. | S.G. (Method) | E.V. |
|---|---|---|---|---|---|---|---|---|
| 15 | 3 | BF$_3$O(C$_2$H$_5$)$_2$ (3 wt %) | 70 | 20 | Cross-linked | — | 1.195 (C) | 1.8% |
| 16 | 3 | BF$_3$O(C$_2$H$_5$)$_2$ (1 wt %) | 30 | 3 | Viscous | c.a. 3000 | 1.140 (C) | 6.7% |
| 17 | 4 | BF$_3$O(C$_2$H$_5$)$_2$ (3 molar %) | 120 | 24 | Solid | c.a. 1000 | 1.21 (C) | 3% |
| 18 | 5 | BF$_3$O(C$_2$H$_5$)$_2$ (3 molar %) | 120 | 24 | Viscous | c.a. 800 | 1.24 (C) | 7% |
| 19 | 6 | BF$_3$—monoethylamine complex (3 wt %) | 150 | 4 | Solid | — | 1.28 (C) | 4% |
| 20 | 7 | BF$_3$—monoethylamine complex (3 wt %) | 150 | 6 | Cross-linked | — | 1.220 (A) | 0% |
| 21 | 10 | BF$_3$—monoethylamine complex (3 wt %) | 150 | 6 | Cross-linked | — | 1.196 (A) | 0.2% |
| 22 | 11 | BF$_3$—monoethylamine complex (3 wt %) | 150 | 6 | Cross-linked | — | 1.200 (A) | 0% |
| 23 | 12 | BF$_3$—monoethylamine complex (3 wt %) | 150 | 6 | Cross-linked | — | 1.257 (A) | 0.1% |
| 24 | 11 | BF$_3$O(C$_2$H$_5$)$_2$ (3 wt %) | 120 | 24 | Cross-linked | — | 1.199 (A) | 0% |
| 25 | 12 | BF$_3$O(C$_2$H$_5$)$_2$ (3 wt %) | 130 | 24 | Cross-linked | — | 1.255 (A) | 0.3% |
| 26 | 9 | BF$_3$—monoethylamine complex (3 wt %) | 180 | 2 | Cross-linked | — | 1.268 (A) | 0.5% |
| 27 | 8 | Stannic chloride (2 wt %) | 150 | 4 | Cross-linked | — | 1.280 (A) | 0.1% |

EXAMPLE 28

To the monomer of 1-ethyl-4-hydroxymethyl-2,6,7-trioxabicyclo[2,2,2] octane was added 2% by weight, based on the monomer, of diphenyliodonium hexafluorophosphate and a sample of the resultant mixture was inserted between Mylar films. This assembly was irradiated ten times with ultraviolet rays at a conveyor speed of 10 m/min. from a distance spaced by 20 cm by means of a high-tension (160 W/cm) mercury lamp (manufactured by Ushio Denki K.K., Japan).

There was thus obtained a flexible transparent solid polymer having a specific gravity of 1.190 (Method C) which indicates an expansion in volume of 1.2%.

EXAMPLE 29

The procedure of Example 28 was repeated but using the monomer of 1-vinyl-4-ethyl-2,6,7-trioxabicyclo[2,2,2] octane. There was thus produced a polymer in the form of rigid transparent film which had a shore hardness of D-52. The specific gravity of the polymer was 1.202 (Method A) indicating a calculated expansion of 1.2%.

EXAMPLE 30

This Example illustrates the cationic polymerization in solution of 1-ethyl-4-hydroxymethyl-2,6,7-trioxabicyclo[2,2,2] octane.

1 g of the monomer compound was dissolved in 5 ml of 1,1-dichloroethane, to which was then added 3 molar %, based on the monomer, of BF$_3$O(C$_2$H$_5$)$_2$ as initiator. The mixture was allowed to polymerize at 30° C. for 48 hours to produce a polymer having a weight average molecular weight of about 800.

EXAMPLE 31

This Example illustrates the radical polymerization of 1-vinyl-4-ethyl-2,6,7-trioxabicyclo[2,2,2] octane prepared as in Example 3.

(i) The monomer was placed in a tube, into which was introduced 3 molar %, based on the monomer, of azobisisobutyronitrile as initiator and the tube was then sealed and heated at 70° C. for 17 hours to effect the polymerization. The polymer produced in a yield of about 28% was separated from the polymerization mixture by subjecting the latter to preparative liquid chromatography on columns of TSK Gel (G-3000 HG+G-2000 HG) using chloroform as eluent at a flow rate of 4 ml/min.

The polymer thus obtained had a weight average molecular weight of c.a. 2000. The infrared spectroscopy of the polymer showed the existence of the absorption at 950 cm$^{-1}$ due to the ether (C—O—CH$_2$) of the bicyclo orthoester group and the disappearance of the absorptions at 990 and 1420 cm$^{-1}$ attributed to the vinyl group which the monomer compound had carried.

(ii) To the monomer placed in a tube was added 3 molar %, based on the latter, of di-t-butylperoxide as initiator and the tube was sealed and heated at 130° C. for 17 hours. The polymer produced in a yield of about 40% was dissolved in tetrahydrofuran and the solution was added dropwise under stirring into n-hexane to precipitate the polymer. The precipitation operation was repeated three times to give a purified polymer in the form of white powder which had an average molecular weight of about 2400 and a specific gravity of 1.210 (Method A) indicating a calculated expansion of 0.5%. The infrared spectroscopy showed that the bicyclo orthoester group remained in the polymer.

(iii) 1 g of 1-vinyl-4-ethyl-2,6,7-trioxabicyclo[2,2,2] octane was dissolved in 5 ml of 1,4-dioxane, to which was then added 3 molar %, based on the monomer, azobisisobutyronitrile and the mixture was heated in a glass sealed tube at 80° C. for 7 hours. There was thus obtained a polymer with a weight average molecular weight of about 1000 in a yield of c.a. 12%.

(iv) The procedure of Example 29 was repeated but using as radical photo-initiator 5% by weight, based on the monomer, of benzoin ethyl ether. The result was the production of a viscous polymer.

EXAMPLE 32

This Example illustrates the usefulness of the compound of Example 1 as a material for adhesives.

An adhesive precursor prepared by adding to the compound of Example 1, 3 molar % of $BF_3O(C_2H_5)_2$ as catalyst was applied onto the surface of a steel or glass plate of 5 mm thick, immediately followed by superposing another steel or glass plate on the treated plate. The assembly was kept aside at 70° C. for one hour and then at 120° C. for 3 hours.

Thereafter, the assembly was tested on its shearing adhesion strength according to the method of JIS K-6850-1976. It was found that the shearing adhesion strength for steel-steel assembly was 120 kg/cm², while there occurred breakdown of the matrix plate for glass-glass assembly.

What we claim is:

1. A bicyclic orthoester compound of the formula

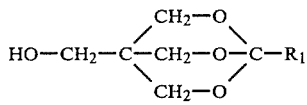
(Ia)

wherein $R_1$ is an alkyl containing 1 to 4 carbon atoms.

2. A compound according to claim 1, in which $R_1$ is methyl.

3. A compound according to claim 1, in which $R_1$ is ethyl.

4. A bicyclic orthoester compound of the formula

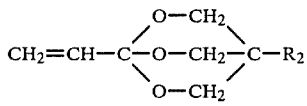
(Ib)

wherein $R_2$ is an alkyl containing 1 to 4 carbon atoms.

5. A compound according to claim 4, in which $R_2$ is ethyl.

6. A bicyclic orthoester compound of the formula

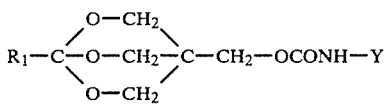

wherein $R_1$ is an alkyl containing 1 to 4 carbon atoms and Y is an organic monoisocyanate residue.

7. A compound according to claim 6, in which $R_1$ is methyl or ethyl.

8. A compound according to claim 6 or 7, in which Y is a substituted or unsubstituted alkyl, aryl, alkenyl, aralkyl, alkaryl or cycloalkyl group, and which may be substituted by one or more of halogen atoms and alkoxy groups.

9. A compound according to claim 8, in which Y is an substituted or unsubstituted alkyl, aryl, aralkyl, alkaryl group which contains up to 12 carbon atoms and which may be substituted by one or more of halogen atoms and alkoxy groups.

10. A compound according to claim 9, in which Y is methyl, ethyl, propyl, hexyl, phenyl, or benzyl.

11. A compound according to claim 10, in which Y is ethyl or phenyl.

12. A bicyclic orthoester compound of the formula

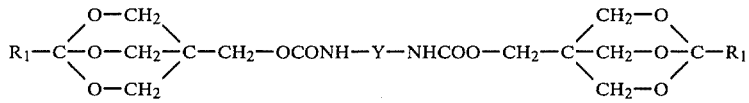

wherein each $R_1$ is an alkyl containing 1 to 4 carbon atoms and Y is an organic diisocyanate residue.

13. A compound according to claim 12, in which $R_1$ and $R_3$ are methyl or ethyl.

14. A compound according to claim 12 or 13, in which Y is a substituted or unsubstituted alkylene, arylene, aralkylene, alkarylene or cycloalkylene group or a group of the formula:

—A—A— or —A—B—A— where each A is a substituted or unsubstituted phenylene or cycloalkylene group, and which may be substituted by one or more of halogen atoms and alkoxy groups and B is an alkylene group or oxygen atom.

15. A compound according to claim 14, in which Y is a group selected from the following:

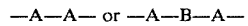

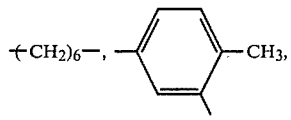

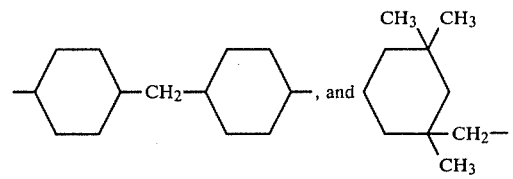

16. A compound of claim 1 which is selected from: 1-ethyl-4-hydroxymethyl-2,6,7-trioxabicyclo[2,2,2] octane; and 1-methyl-4-hydroxymethyl-2,6,7-trioxabicyclo[2,2,2] octane.

17. A compound of claim 4 which is 1-Vinyl-4-ethyl-2,6,7-trioxabicyclo[2,2,2] octane.

18. A compound of claim 6 which is selected from: 1-ethyl-4-ethylcarbamoyloxymethyl-2,6,7-trioxabicyclo[2,2,2] octane;
1-ethyl-4-phenylcarbamoyloxymethyl-2,6,7-trioxabicyclo[2,2,2] octane; and
1-methyl-4-phenylcarbamoyloxymethyl-2,6,7-trioxabicyclo[2,2,2] octane.

19. A compound of claim 12 which is selected from: the compound of the formula Q—(CH₂)₆—Q;
the compound of the formula the compound of the formula
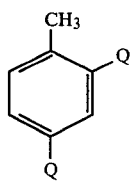
the compound of the formula
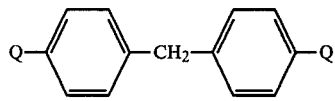
the compound of the formula
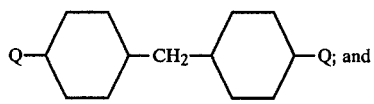
the compound of the formula
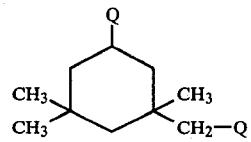
where each Q stands for the group of the formula
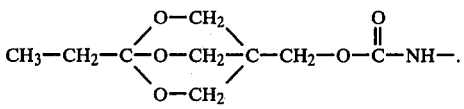
* * * * *